United States Patent
Gerwig et al.

(10) Patent No.: US 10,412,784 B2
(45) Date of Patent: Sep. 10, 2019

(54) FIELD DEVICE FOR USE IN HYGIENIC APPLICATIONS IN PROCESS- AND AUTOMATION TECHNOLOGY AND METHOD FOR ITS MANUFACTURE

(71) Applicant: Endress+Hauser GmbH+Co. KG, Maulburg (DE)

(72) Inventors: Simon Gerwig, Schopfheim (DE); Raphael Schonhardt, Rehinfelden (DE); Torsten Weinstein, Zell (DE)

(73) Assignee: Endress+Hauser SE+Co. KG, Maulburg (DE)

( * ) Notice: Subject to any disclaimer, the term of this patent is extended or adjusted under 35 U.S.C. 154(b) by 0 days.

(21) Appl. No.: 15/738,679

(22) PCT Filed: May 24, 2016

(86) PCT No.: PCT/EP2016/061686
§ 371 (c)(1),
(2) Date: Dec. 21, 2017

(87) PCT Pub. No.: WO2016/206899
PCT Pub. Date: Dec. 29, 2016

(65) Prior Publication Data
US 2018/0192475 A1 Jul. 5, 2018

(30) Foreign Application Priority Data
Jun. 23, 2015 (DE) .......... 10 2015 110 092

(51) Int. Cl.
*F25B 29/00* (2006.01)
*F25D 21/00* (2006.01)
(Continued)

(52) U.S. Cl.
CPC .......... *H05B 1/023* (2013.01); *G01N 25/66* (2013.01); *H05B 2203/035* (2013.01)

(58) Field of Classification Search
CPC .. H05B 1/023; H05B 2203/035; G01N 25/66; A61M 16/1075; A61M 16/0051; A61M 2016/0027; A61M 16/0816
(Continued)

(56) References Cited

U.S. PATENT DOCUMENTS 5,806,763 A    9/1998  Jones
9,265,902 B2 *  2/2016  Payton .............. A61M 16/1075
(Continued)

FOREIGN PATENT DOCUMENTS

DE    102006032250 A1    1/2008
DE    102009003090 A1    11/2010
(Continued)

OTHER PUBLICATIONS

Search Report for German Patent Application No. 10 2015 110 092.4, German Patent Office, dated Jan. 7, 2016, 5 pp.
(Continued)

*Primary Examiner* — David D Hwu
(74) *Attorney, Agent, or Firm* — Kelly J. Smith; PatServe

(57) ABSTRACT

A field device for use in hygienic applications in process and automation technology is disclosed, including a sensor element, an electrical circuit, a heating element, a housing, having an outside and an inside in which the sensor element, the electrical circuit and the heating element are arranged and mounted, and an external energy supply unit, wherein the field device possesses two connection pins, to which the sensor element and the electrical circuit are connected and enabling an electrical connection with the external electrical current supply, whereby forming a first electrical current loop, and wherein a second electrical current loop is arranged such that the heating element is in electrical contact with the external energy unit via one of the two connection pins and a third connection pin, whereby the second electrical current loop forms a parallel circuit with the first electrical current loop.

11 Claims, 2 Drawing Sheets

(51) Int. Cl.
*F28F 17/00* (2006.01)
*H05B 1/02* (2006.01)
*G01N 25/66* (2006.01)

(58) Field of Classification Search
USPC .......................................................... 165/233
See application file for complete search history.

(56) References Cited

U.S. PATENT DOCUMENTS

2002/0162829 A1   11/2002  Weber et al.
2014/0045191 A1*   2/2014  DeJohn .................. C12Q 1/686
                                                                       435/6.12

FOREIGN PATENT DOCUMENTS

| DE | 102013012434 A1 | 1/2014 |
| DE | 102013108531 A1 | 2/2015 |
| EP | 1445984 A2 | 8/2004 |
| EP | 1860513 A2 | 11/2007 |
| EP | 1865440 A1 | 12/2007 |

OTHER PUBLICATIONS

International Search Report for Patent Application No. PCT/EP2016/061686, WIPO, dated Sep. 7, 2016, 14 pp.

* cited by examiner

FIELD DEVICE FOR USE IN HYGIENIC APPLICATIONS IN PROCESS- AND AUTOMATION TECHNOLOGY AND METHOD FOR ITS MANUFACTURE

CROSS-REFERENCE TO RELATED APPLICATIONS

The present application is related to and claims the priority benefit of German Patent Application No. 10 2015 110 092.4, filed on Jun. 23, 2015 and International Patent Application No. PCT/EP2016/061686 filed on May 24, 2016, the entire contents of which are incorporated herein by reference.

TECHNICAL FIELD

The invention relates to a field device for use in hygienic applications in process- and automation technology and to a method for manufacture of such a field device. The field device includes, in such case, at least one sensor element for registering a first physical, measured variable, at least one electrical circuit for transducing the measured variable registered by the sensor element into a measurement signal, at least one heating element, at least one housing, which has an outside and an inside and in which at least the sensor element, the electrical circuit and the heating element are arranged and mounted, and an external energy supply unit.

BACKGROUND

Known from the state of the art are field devices, which are used in industrial plants. In process automation technology, same as in the manufacturing automation technology, field devices are often applied. Referred to as field devices are, in principle, all devices, which are applied near to the process and which deliver, or process, process relevant information. Thus, field devices are used for registering and/or influencing process variables. Serving for registering process variables are measuring devices and their sensors. These are used, for example, for pressure- and temperature measurement, conductivity measurement, flow measurement, fill level measurement, etc. and register the corresponding process variables, pressure, temperature, conductivity, pH-value, fill level, flow etc. Used for influencing process variables are actuators. These are, for example, pumps or valves, which can influence the flow of a liquid in a pipe or the fill level in a container. Besides the above mentioned measuring devices and actuators, also referred to as field devices are remote I/Os, radio adapters, and, in general, devices, which are arranged at the field level.

A large number of such field devices are produced and sold by the Endress+Hauser group of companies.

Many field devices for process automation are exposed to various environmental influences, depending on their location of use. In different branches of industry, different environmental conditions prevail, requiring appropriately different protective measures.

In process automation, especially in hygienic applications, processes are frequently run, in which high humidity is present. Steam deposits as condensate on surfaces of the process plant. This condensate can damage the plant and especially the field devices located therein. Field devices with metal housings can corrode from longer contact with water. If steam gets into the interior of the housing and condenses there, the functionality of the field device can be degraded. For example, condensate can accumulate on the electronics and cause defects and/or corrosion. Furthermore, short-circuits between the electronics and the housing, caused by the moisture, can arise and limit the ability of the field devices to function.

Pressure measuring devices, especially relative pressure measuring devices, require a reference air duct for correct operation. This is led into the housing and is in contact with the environment by means of a pressure equalizing element. If condensate deposits on this pressure equalizing element, then, in given cases, the air supply into the reference air duct is blocked. As consequence, defective pressure values are measured.

Condensate occurs when the temperature subceeds a threshold temperature, the so-called dewpoint temperature, also referred to as the dew point. The dewpoint temperature of a gas mixture is determined by the percentage of a condensable component. The gas mixture can be, for example, air, in the case of which the condensable component is water. The higher the percentage of the condensable component in the gas mixture, the lower is the dewpoint temperature.

If a process has one or more phases with low process temperatures, for example, cooling phases, then in these phases there is increased danger of condensation.

An opportunity for protecting field devices from condensation is to change the dimensions of the housing. With a greater housing length, sensitive components, such as, for example, the electronics or the pressure equalization element in the case of pressure measuring devices can be located removed from the process connection, so that low temperature does not reach these components. This is, however, associated with increased material costs. Moreover, space is limited in many process plants, so that the housing dimensions have to be as small as possible.

Another possibility is to decouple the process temperature from the sensitive components. This is done via so-called temperature decouplers. Temperature decouplers are housing sections with special forms, for example, ribs or constrictions. Disadvantages of this method are, depending on form of embodiment, a low efficiency and increased effort in the case of the housing development.

An effective technique for avoiding condensate on the housing is to keep the temperature of the housing higher than the dewpoint temperature.

DE102013108531A1 describes a field device with integrated heating element and temperature control loop. This field device is applied in the case of very low temperatures in the range of −40° C. to −60° C.; the heating element, in such case, protects temperature sensitive components, such as, for example, microcontrollers, from failing due to these lows temperatures. Disadvantages of this technique are in the increased effort involved with the control loop, the additional manufacturing costs and the increased electrical current consumption.

SUMMARY

An object of the invention is to provide a field device, which is safe to use in environments with high condensation danger.

The object is achieved by a field device for use in hygienic applications in process- and automation technology, comprising at least one sensor element for registering a first physical, measured variable, at least one electrical circuit for transducing the measured variable registered by the sensor element into a measurement signal, at least one heating element, at least one housing, which has an outside and an inside and in which at least the sensor element, the electrical circuit and the heating element are arranged and mounted, and an external energy supply unit, wherein the field device possesses two connection pins, to which the sensor element and the electrical circuit are connected and via which there is an electrical connection with the external electrical current supply, whereby a first electrical current loop is formed and wherein a second electrical current loop is provided, which is so arranged that the heating element is in electrical contact with the external energy unit via one of the two connection pins and a third connection pin, whereby the second electrical current loop forms a parallel circuit with the first electrical current loop.

This solution provides a cost effective implementing of the heating element. By direct connection of the heating element to the electrical current supply unit, no additional energy sources are required. The parallel circuit of the electronics with the heating element assures a reliable functioning of field device, since the operation of the heating element causes no changes of the measurement results.

An advantageous embodiment provides that the heating element is composed of at least one electronic component. Electrical current flow through the component provides heat, which heats the housing. Application of standard electronic components means that the manufacturing process of the integrated heating element is cost effective.

An advantageous embodiment provides that the heating element is an SMD-resistor or a parallel circuit of at least two SMD-resistors. Furthermore, the heating element can also be a field effect transistor or a plurality of field effect transistors or similar electronic components.

A preferred embodiment provides that the heating element is arranged in the housing in such a manner that heat exchange between the heating element and the housing occurs conductively. For such purpose, the heating element is placed in contact with the housing. The heat produced by the heating element is led directly into the housing.

A preferred embodiment provides that the heating element is arranged in the housing in such a manner that the heat exchange between the heating element and the housing occurs convectively. For such purpose, the heating element is located in the inner space of the housing. The heat radiates from the heating element and can be used to heat, besides the housing, also the electronics unit.

A preferred embodiment provides that the first electrical current loop is a 4-20 mA electrical current loop.

An especially preferred form of embodiment provides that the first electrical current loop is a digital communication, which communicates by means of a fieldbus protocol of process- and automation technology. The bus protocol can be, in such case, for example, a Profibus® PA-, Foundation Fieldbus®-, ModBus®- or HART® protocol.

An especially preferred embodiment provides that the field device is a pressure measuring device. As already described, pressure measuring devices are extremely error susceptible, for example, because of a blocking of the reference air supply. The present invention offers the great advantage of reducing such susceptibility to error, thus, improving the reliability of pressure measuring devices.

The object of the invention is further achieved by a method for manufacturing a field device for use in hygienic applications in process- and automation technology, wherein the heating element is supplied with energy via the second electrical current loop, whereby the heating element is heated and heat is transferred to the housing, and wherein the housing temperature rises above the dewpoint temperature, so that the forming from condensate on the outside and on the inside of the housing is prevented.

In a preferred embodiment of the method, the heating element is manually turned on. This can be achieved, for example, by means of a hardware solution, such as a switch, which is located on the outside of the housing of the field device or on the process plant, however, also by means of a software solution. With a manual switch, energy can be saved, since the heating element is then operated only when it is required.

In an especially preferred embodiment of the method, the heating element is turned on only in process phases, in which the process temperature lies below the dewpoint temperature. This is the case, for example, in cooling phases of the process.

BRIEF DESCRIPTION OF THE DRAWINGS

The invention will now be explained in greater detail based on the appended drawing, the figures of which show as follows:

FIG. 2 shows a schematic drawing of a circuit of a field device with heating turned on.

DETAILED DESCRIPTION

Figure 1:
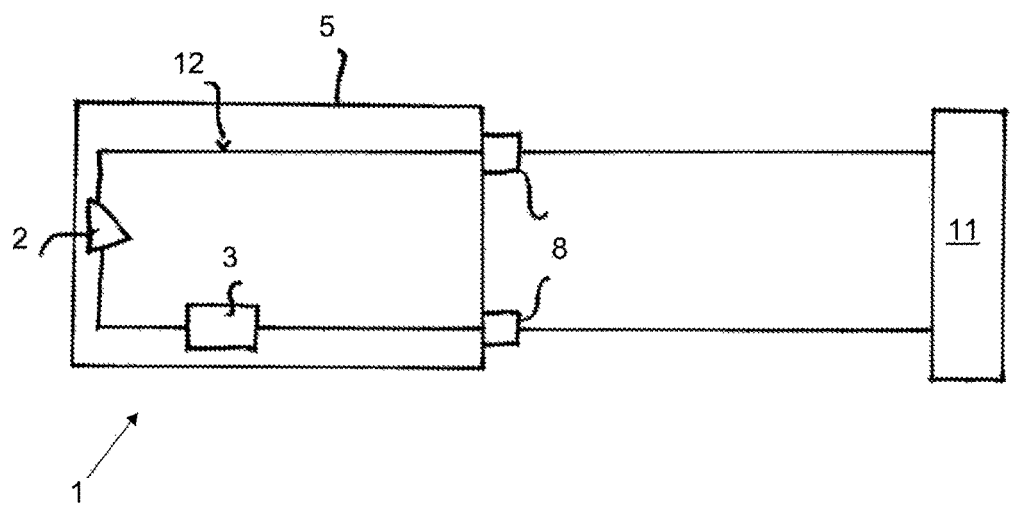
FIG. 1 shows a schematic drawing of a circuit of a field device of the invention in the standard mode.

FIG. 1 shows a schematic drawing of a circuit of a field device 1 in standard operation. Field devices, especially sensors and/or actuators, are frequently operated in a 2-conductor mode. The energy supply of the field devices occurs via an external energy unit, which is connected by means of an M12x1—or valve connector to connection pins 8, which are exposed on the housing. Such connector versions offer, according to standard, connection opportunities for up to four connection pins.

Located in the interior of the housing 5 are a sensor element 2 and an electrical circuit 3 connected to the connection pins 8. In this way, a first electrical current loop 12 is formed. This first electrical current loop can be, for example, a 4-20 mA electrical current loop or a communication network.

Sensor element 2 registers a physical, measured variable. The electrical circuit 3 transduces this measured variable then into a measurement signal. The measurement signal is output via one of the two connection pins 8 and can be registered or further processed, for example, in additional units of the network.

Figure 2:
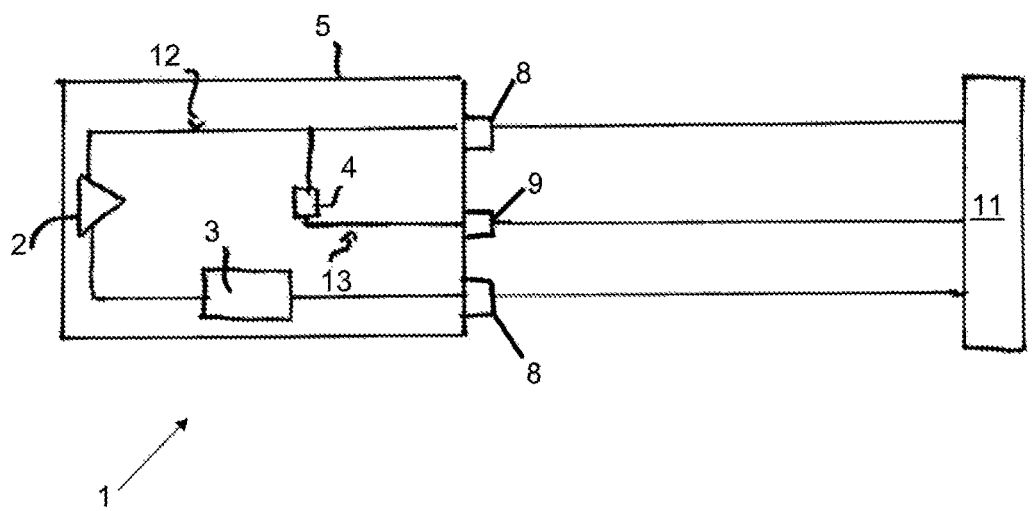

FIG. 2 shows a schematic drawing of a circuit of a field device with turned on heating. Many field devices, for example, the relative pressure measuring device, Cerabar PMP23, which is produced and sold by the applicant, possess in the plant an additional, third connection pin 9, which offers, in special embodiments of the device, connection opportunities for particular functions, but which, in the standard embodiment, goes unused. A heating element 4 is placed in the inner space of the housing 5 and connected with one of the two connection pins 8 and the third connection pin 9. In this way, the heating element 4 is, same as the sensor element 2 and the electrical circuit 3, connected to the external energy unit 11 and draws energy from this. By connection to the third connection pin 9, a second electrical current loop 13 is formed, which forms a parallel circuit with the first electrical current loop 12. The device is, in this way, operated in a 3-conductor mode. The connection of the connection pins 8 and the third connection pin 9 occurs also here by means of an M12x1—or valve connector.

The parallel circuit assures that the electrical current supply of the sensor element 2 and the electrical circuit 3 in the first current loop 12 is not degraded upon the switching of the heating element 4 on. In designing the plant, it must, however, be heeded that the energy required from the external energy unit 11 is greater in the case of switched-on heating element 4 than in the standard operation.

Figure 3:
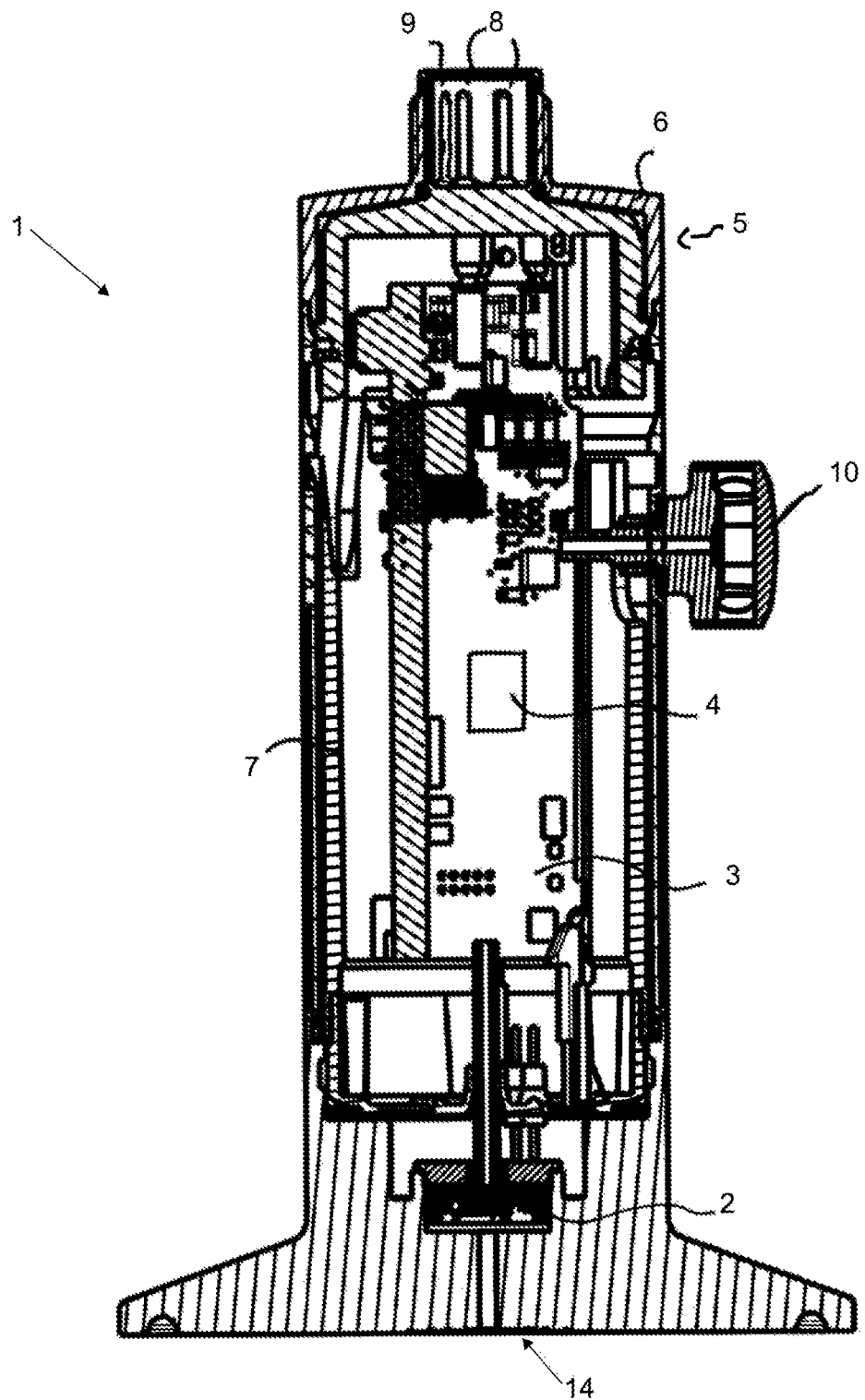
FIG. 3 shows a drawing of an example of an embodiment of a field device of the invention.

FIG. 3 shows a drawing of an example of an embodiment of a field device 1 of the invention in the form of a relative pressure measuring device. Mounted on housing 5 is a pressure equalizing element, with whose help the reference air supply for the sensor is enabled. The heating element 4 is in this example placed on the circuit board of the electrical circuit 3, so that the heat exchange with the housing occurs convectively. A variant of this type of embodiment provides that the heating element 4 is connected directly with the housing 5, so that the heat exchange occurs conductively.

If the process is in a cooling phase, then there reigns on the process connection a low temperature, which propagates to the entire housing 5. If the temperature of the housing 5 sinks below the dewpoint temperature, then condensation can accumulate on the outside 6 and on the inside 7 of the housing. If condensate covers the pressure equalizing element 10, then, in given cases, the reference air supply is blocked, whereby defective measured values are to be reckoned with.

In such a case, the heating element 4 is turned on, which is connected with the external energy unit 11 via one of the connection pins 8 and the third connection pin 9. In this way, the housing is easily heated. As soon as the temperature of the housing 5 rises above the dewpoint temperature, the condensate begins to evaporate and further condensate formation is prevented. Ideally, the heating element 4 should be turned on a short time before the beginning of a process cooling phase, in order to prevent condensate formation from the beginning.

The invention claimed is:

1. A field device for use in hygienic applications in process and automation technology, comprising:
   at least one sensor element embodied to register a measured variable;
   at least one electrical circuit configured for transducing the measured variable registered by the sensor element into a measurement signal;
   at least one heating element;
   at least one closed housing, having an outside and an inside, in which at least the sensor element, the electrical circuit and the heating element are disposed and mounted; and
   first and second connection pins connected to the sensor element and the electrical circuit, via which the sensor element and the electrical circuit are electrically connected with an external energy supply unit, thereby forming a first electrical current loop,
   wherein a second electrical current loop is formed such that the heating element is in electrical contact with the external energy supply unit via one of the first and second connection pins and a third connection pin, wherein the first, second, and third connection pins are distinct, wherein the second electrical current loop forms a parallel circuit with the first electrical current loop.

2. The field device of claim 1, wherein the heating element includes at least one electronic component.

3. The field device of claim 1, wherein the heating element is an SMD-resistor or a parallel circuit of at least two SMD-resistors.

4. The field device of claim 1, wherein the heating element is disposed in the closed housing such that heat exchange between the heating element and the closed housing occurs conductively.

5. The field device of claim 1, wherein the heating element is disposed in the closed housing such that heat exchange between the heating element and the closed housing occurs convectively.

6. The field device of claim 1, wherein the first electrical current loop is a 4 to 20 milliamp electrical current loop.

7. The field device of claim 1, wherein the first electrical current loop includes a digital communication, which communicates using a fieldbus protocol of process and automation technology.

8. The field device of claim 1, wherein the field device is a pressure measuring device.

9. A method for manufacturing a field device for use in hygienic applications in process and automation technology, comprising:
   arranging at least one sensor element, at least one electrical circuit and at least one heating element within a closed housing;
   forming a first electrical current loop by electrically connecting the at least one sensor element and the at least one the electrical circuit with an external energy supply unit via first and second connection pins, the at least one sensor element embodied to register a measured variable, the at least one electrical circuit configured for transducing the measured variable registered by the sensor element into a measurement signal; and
   forming a second electrical current loop by electrically connecting the heating element with the external energy supply unit via one of the first and second connection pins and a third connection pin, wherein the first, second, and third connection pins are distinct, wherein the second electrical current loop forms a parallel circuit with the first electrical current loop, and wherein, in operation:
      the heating element is supplied with energy via the second electrical current loop such that the heating element is heated and heat is transferred to the closed housing; and
      a temperature of the closed housing rises above a dewpoint temperature of the application such that condensation formation on an outside and an inside of the closed housing is prevented.

10. The method of claim 9, wherein, in operation, the heating element is manually turned on.

11. The method of claim 9, wherein, in operation, the heating element is turned on only in process phases in which a temperature of the process falls below a dewpoint temperature of the process phase.

* * * * *